United States Patent [19]

De Clercq et al.

[11] Patent Number: 4,988,678
[45] Date of Patent: Jan. 29, 1991

[54] COMBINATIONS OF FU AND BVU AS ANTI-ADENOCARCINOMA AGENTS

[75] Inventors: Erik De Clercq, Leuven, Belgium; Masaaki Iigo, Kitamoto, Japan

[73] Assignee: Stichting Rega VZW, Leuven, Belgium

[21] Appl. No.: 373,824

[22] Filed: Jun. 29, 1989

Related U.S. Application Data

[62] Division of Ser. No. 154,193, Feb. 11, 1988, Pat. No. 4,894,365.

[30] Foreign Application Priority Data

Feb. 13, 1987 [NL] Netherlands .................. 8700366

[51] Int. Cl.$^5$ .................. A61K 31/70; A61K 31/505
[52] U.S. Cl. ........................ 514/50; 514/274
[58] Field of Search ....................... 514/50, 274

[56] References Cited

U.S. PATENT DOCUMENTS 4,650,801 3/1987 Fujii et al. ................ 514/274

FOREIGN PATENT DOCUMENTS 2016921A 9/1979 United Kingdom ............ 514/274

OTHER PUBLICATIONS

Chester et al., Chemotherapy of Cot, 2nd Ed., John Wiley & Sons, N.Y., N.Y., (1981), pp. 77–78.
Effect of (E)-5-(2 Bromovinyl) Uracil on the Catabolism and Antitumor Activity of 5-Fluorouracil in Rats and Leukemic Mice, Can. Res. 46, 1094–1101, 1986.
Potential of Bromovinyl Deoxyuridine in Anticancer Chemotherapy Clercq., Anticancer Res. 6, 549–556 (1986).
C. Desgranges et al., Nucleric Acid Research, 12, 2081–2090 (1984).
C. Desgranges et al., Cancer Research, 46, 1094–1101 (1986).
E. De Clercq, Anticancer Research, 6, 549–556 (1986).
E. De Clercq, Verhandelingen Kon. Acad. Geneeskunde Belgie, 48, 261–290 (1986).
Iigo et al., *Japan Journal of Cancer Research* (Gann), 78, 409–413, (1987).
Iigo et al., *Eur. Journ. Cancer Clin. Oncol.*, 23, 773–777 (1987).
Iigo et al., *Biochem. Pharmacol.*, 37, 1609–1613, (1988).

Primary Examiner—Merrell C. Cashion, Jr.
Assistant Examiner—G. S. Kishore
Attorney, Agent, or Firm—Birch, Stewart, Kolasch & Birch

[57] ABSTRACT

The antitumor activity of 5-fluorouracil and its precursors against adenocarcinomas can be potentiated without a corresponding increase in toxicity by combining these compounds with (E)-5-(2-bromovinyl)-uracil or a precursor thereof. The combinations may have the form of a single composition or two separate compositions.

8 Claims, 1 Drawing Sheet

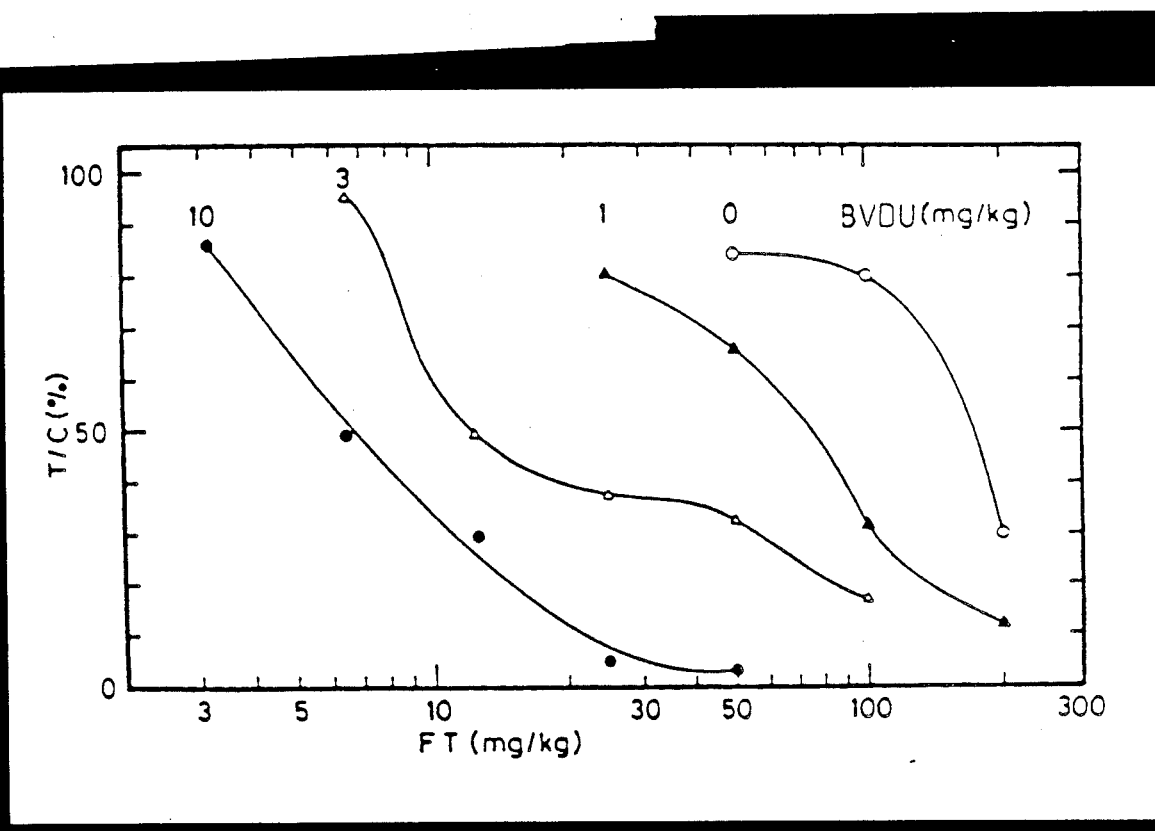

COMBINATIONS OF FU AND BVU AS ANTI-ADENOCARCINOMA AGENTS

This application is a divisional of copending application Ser. No. 07/154,193, filed on Feb. 11, 1988 now U.S. Pat. No. 4,894,365.

The present invention relates to an antitumor agent having activity against adenocarcinoma tumors and is based upon a combination of a well-known antitumor agent with an activity-potentiating agent.

The compound 5-fluorouracil (abbreviated FU) is a well-known antitumor agent used in the treatment of various cancers, in particular adenocarcinomas in the breast and gastrointestinal tract. The margin between activity and toxicity of FU is, however, very narrow and moreover, FU is degraded rather rapidly in the liver.

In some countries, ftorafur (abbreviated FT), i.e. $N_1$-(2'-tetrahydrofuryl)-5-fluorouracil is used instead of FU. Ftorafur has a similar activity as FU and a lower toxicity since it is converted slowly to FU in the human body. Nevertheless, the margin between activity and toxicity of ftorafur is still narrow and thus, there exists a need for agents having a wider margin in this respect.

During experiments which led to the invention, it has now been found that the antitumor activity of FU or FT against adenocarcinomas may be potentiated without a corresponding increase in toxicity by combining this compound with (E)-5-(2-bromovinyl)-2'-deoxyuridine (abbreviated BVDU).

BVDU is a potent and selectively acting antiviral agent, which in particular is active against infections caused by herpes simplex virus type 1, varicella zoster virus and Epstein-Barr virus. In the human body, it is rapidly converted to 5-(2-bromovinyl)uracil (abbreviated BVU) which remains present in the blood stream for a relatively long period. BVU as such is inactive against replication of viruses but it is responsible for the potentiation of the antitumor activities of FU or FT.

When BVDU is combined with FU or FT, the antitumor activity against adenocarcinomas thereof is potentiated substantially whilst the toxicity of FU/FT increases to a lesser degree. This means that the useful margin as well as the therapeutic index of FU/FT increases significantly. In fact, BVU is responsible for this potentiation and therefore, a similar effect will occur with combinations of FU/FT with BVU and with substances other than BVDU that are converted to BVU in the human body. Thus, potentialities are offered for an efficient control of adenocarcinomas in man.

It should be noted that a potentiated activity of FU against leukemia in mice by means of BVU has been disclosed already by Desgranges et al. in Cancer Research, 46, 1094–1101 (1986). However, tests made by Desgranges et al showed that the toxicity of FU was also potentiated by BVU. These data did not allow to a presumption that the activity of FU/FT against adenocarcinomas would be susceptible of potentiation by BVU without a corresponding increase in toxicity.

The invented agent may be a single therapeutic composition which comprises a combination of FU/FT with BVU (or a precursor of BVU), but it may also comprise two separate compositions which are to be administered in combination, viz. a FU/FT-containing composition and a composition containing BVU or BVU precursor. The compositions may have the form of suspensions, solutions and the like and may be used for oral or parenteral administration. They may be prepared by mixing the active ingredients with pharmaceutically acceptable excipients of inert nature, such as aqueous or non-aqueous solvents together with stabilisers, emulsifiers, additives and the like. The concentration of the active ingredient in any composition may vary between 0.1% and 100%, dependent from the route of administration. The ratio between FU/FT and BVU or BVU-precursor may be between 1:1 and 1:100. Further, the daily dose of the active ingredients to be administered may be between 0.1 mg and 100 mg per kg of body weight.

The invention is further illustrated by the following Examples which are not meant to be restrictive of the invention. Reference is made to the drawing which is a graphical representation of the results of Example 2. The abbreviations used are the same as in the preceding description.

The compounds FU and FT as used in the Examples were commercially obtained and the compound BVDU was synthesized according to the method disclosed by Jones et al., Tetrahedron Letters, 4415–4418 (1979).

Example 1

Groups of 6 male $BDF_1$-mice having a body weight of 21 to 23 g, were subcutaneously inoculated on day 0 with tumor cells of the type adenocarcinoma 755 at a dose of $5=10^5$ cells per mouse. Thereupon, the compound FU (or a combination of FU and BVDU) was perorally administered in a predetermined daily dose during 5 consecutive days, starting 24 hours after the inoculation with tumor cells. On day 12, the tumor weight was determined and compared with the tumor weight in a non-treated control group. The doses of the active compounds as used, as well as the average tumor weight and the percent tumor weight with regard to the control groups (T/C) are represented in the following Table.

| Compounds | Mean ± SD (mg) | T/C (%) |
|---|---|---|
| Control | 2076 ± 364 | — |
| FU, 5 mg/kg | 2523 ± 389 | 122 |
| FU, 10 mg/kg | 1759 ± 726 | 85 |
| FU, 20 mg/kg | 675 ± 355 | 32 |
| FU, 30 mg/kg | Toxic (3/6 died) | |
| FU, 1 mg/kg + BVDU, 100 mg/kg | 1355 ± 561 | 65 |
| FU, 3 mg/kg + BVDU, 100 mg/kg | 486 ± 298 | 23 |
| FU, 5 mg/kg + BVDU, 100 mg/kg | 288 ± 210 | 14 |
| FU, 10 mg/kg + BVDU, 100 mg/kg | 0 ± 0 (1/6 died) | 0 |
| FU, 20 mg/kg + BVDU, 100 mg/kg | Toxic (4/6 died) | |
| FU, 30 mg/kg + BVDU, 100 mg/kg | Toxic (6/6 died) | |

From the Table, the following values for the therapeutic index may be calculated, based upon the ratio of $LD_{50}$ (50% lethal dose) to $ED^{50}$ (50% effective dose, that is a dose causing a 50% reduction of T/C):

For FU when used alone: 30/15=2.

For FU when used in combination with BVDU: 17:1.7=10.

This represents a significant increase in therapeutic index of FU.

EXAMPLE 2

Groups of 6 male $BDF_1$ mice having a body weight of 21 to 23 g were subcutaneously inoculated on day 0 with tumor cells of the type adenocarcinoma 755 at a dose of $5=10^5$ cells per mouse. Thereupon, combinations of FT with BVDU were perorally administered in a predetermined daily dose during 5 consecutive days, starting 24 hours after the inoculation with tumor cells. The BVDU was used after dissolution in a physiological saline solution and the FT was used after suspension in 0.5% carboxymethyl cellulose solution. A volume of 0.1 ml per 20 g of body weight was used each time for oral administration. The tumor weight was determined on day 12 and compared with that of the control group which had not been treated with the compounds. The results are represented in the drawing, wherein T/C is the percent ratio of tumor weights in the treated and non-treated groups. The dose of FT has been shown on the abscissa and the doses of BVDU have been indicated at each separate curve.

It appears from the drawing that within the range of doses used (1–10 mg/kg) the antitumor activity of FT was markedly potentiated by BVDU so that a combination of FT at 10 mg/kg with BVDU at 10 mg/kg was as effective as FT alone at 200 mg/kg.

What we claim is:

1. A medicine for the treatment of adenocarcinomas, comprising an effective amount of an active ingredient to reduce adenocarcinoma tumor weight, in a patient ingredient being selected from the group consisting of 5-fluorouracil and $N_1$-(2'-tetrahydrofuryl)-5-fluorouracil, in combination with an effective amount of an ingredient to potentiate the antitumor activity of said active ingredient, said potentiating ingredient being selected from the group consisting of (e)-5-(2-bromobinyl)-uracil and (E)-5-(2-bromovinyl)-2'-deoxyuridine, and a pharmaceutically acceptable carrier therefor.

2. The medicine as claimed in claim 1, which comprises an effective antitumor amount of 5-fluorouracil in combination with an effective potentiating amount of (E)-5-(2-bromovinyl)-2'-deoxyuridine, and a pharmaceutically acceptable carrier therefor.

3. The medicine as claimed in claim 1, which comprises an effective antitumor amount of $N_1$-(2'-tetrahydrofuryl)-5-fluorouracil in combination with an effective potentiating amount of (E)-5-(2-bromovinyl)-2-40-deoxyuridine and a pharmaceutically acceptable carrier therefor.

4. The medicine as claimed in claim 1, which comprises an effective antitumor amount of 5-fluorouracil in combination with an effective potentiating amount of (E)-5-(2-bromovinyl) uracil and a pharmaceutically acceptable carrier therefor.

5. The medicine as claimed in claim 1, which comprises an effective antitumor amount of $N_1$-(2'-tetrahydrofuryl)-5-fluorouracil in combination with an effective potentiating amount of (E)-5-(2-bromonvinyl)-uracil, and a pharmaceutically acceptable carrier therefor.

6. The medicine as claimed in claim 1, which is in the form of a single composition comprising said active ingredient together with said potentiating ingredient and said carrier.

7. The medicine as claimed in claim 1, which is in the form of two separate compositions, one of said two compositions comprising an effective antitumor amount of said active ingredient and a pharmaceutically acceptable carrier therefor, and a second of said two compositions comprising an effective amount of said potentiating ingredient and a pharmaceutically acceptable carrier therefor.

8. The medicine as claimed in claim 1, wherein said active ingredient and said potentiating ingredient are present in a ratio of between 1:1 and 1:100.

* * * * *